United States Patent
Evers et al.

[11] 3,931,270
[45] Jan. 6, 1976

[54] PROCESS FOR PRODUCING 2-THIA SUBSTITUTED 1,4 DIONES

[75] Inventors: William J. Evers, Middletown; Bernard J. Mayers, Cliffwood Beach, all of N.J.

[73] Assignee: International Flavors & Fragrances Inc., New York, N.Y.

[22] Filed: Jan. 7, 1975

[21] Appl. No.: 539,092

Related U.S. Application Data

[63] Continuation-in-part of Ser. No. 386,452, Aug. 7, 1973, abandoned.

[52] U.S. Cl. .......................... 260/455 R; 260/609 R
[51] Int. Cl.² ....................................... C07C 153/07
[58] Field of Search ................................ 260/455 R

[56] References Cited
UNITED STATES PATENTS

| | | | |
|---|---|---|---|
| 2,630,452 | 3/1953 | Crunch et al. ................. | 260/455 R |
| 3,441,589 | 4/1969 | Oswald ............................. | 260/455 R |

OTHER PUBLICATIONS
Reid text, Vol. 4 pp. 15–16. (1962).

*Primary Examiner*—Lewis Gotts
*Assistant Examiner*—D. R. Phillips
*Attorney, Agent, or Firm*—Arthur L. Liberman, Esq.; Harold Haidt, Esq.

[57] ABSTRACT

Process for producing 3-thia substituted alkane 1,4 diones comprising the steps of:
i. Providing a 2-ene-1,4 dione having the structure:

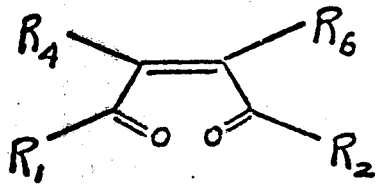

ii. Intimately admixing said 2-ene-1,4 dione with a sulfur compound having the formula:

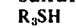

$R_3SH$
thereby providing a substituted or sunsubstituted 2-thia substituted alkane 1,4 dione having the structure:

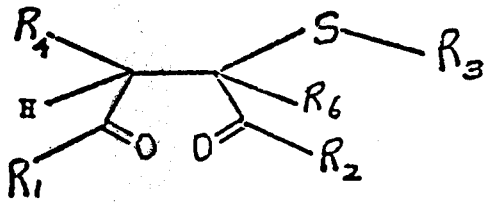

wherein
$r_3$ is selected from the group consisting of acyl and royl, wherein $R_2$ is lower alkyl; and wherein $R_1$, $R_4$ and $R_6$ are the same or different and are selected from the group consisting of hydrogen and lower alkyl; wherein when $R_1$ is hydrogen, the reaction (ii) is carried out in the presence of an organic base; and wherein when $R_1$ is lower alkyl, the reaction (ii) is carried out in the absence of catalyst. Examples of such organic bases are piperidine, pyridine, triethyl amine, quinoline or alpha-picoline.

7 Claims, No Drawings

PROCESS FOR PRODUCING 2-THIA SUBSTITUTED 1,4 DIONES

This application is a continuation-in-part of co-pending application for U.S. Pat. No. 386,452 filed on Aug. 7, 1973 now abandoned.

BACKGROUND OF THE INVENTION

The present invention relates to novel processes for producing 3-thia substituted alkane 1,4-diones.

Artifical flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainity as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the magnetism for flavor development in many foods is not understood. This is noteable in products having meaty and roasted flavor characteristics. It is also noteable in products having vegetable-like and hydrolyzed vegetable protein-like and anise-like flavor characteristics.

Reproduction of roasted and meat flavors and aromas and vegetable-like and hydrolyzed vegetable protein-like and anise-like flavors and aromas has been the subject of the long and continuing search by those engaged in the production of foodstuffs. The severe shortage of foods, especially protein foods, in many parts of the world has given rise to the need for utilizing non-meat sources of proteins and making such proteins as palatable and as meatlike as possible. Hence, materials which will closely simulate or exactly reproduce the flavor and aroma of roasted meat products and liver products and vegetable products are required.

Moreover, there are a great many meat containing or meat based foods presently distributed in a preserved form. Examples being condensed soups, dry-soup mixes, dry meat, freeze-dried or lyophilized meats, packaged gravies and the like. While these products contain meat or meat extracts, the fragrance, taste and other organoleptic factors are very often impaired by the processing operation and it is desirable to supplement or enhance the flavors of these preserved foods with versatile materials which have either roasted meat or gravy-like or vegetable-like or meat-like or ham-like nuances.

2-Alkylfuran-3-thiols and bis-(alkyl-3-furyl) disulfides are disclosed in U.S. Pat. No. 3,723,475 issued on Mar. 27, 1973 to supply meaty flavor aroma and taste nuances to foodstuffs. 2-thia substituted-1,4-diones are disclosed in U.S. Pat. No. 3,836,563 issued on Sept. 17, 1974 to also supply meaty flavors to foodstuffs.

Swiss Pat. No. 531,313 discloses the addition of hydrogen sulfide across a double bond, eliminating the double bond.

Such a reaction, however, is not shown in conjunction with a chemical compound which has two ketone moieties.

The mechanism of the addition of hydrogen sulfide across a double bond of an alpha-beta-unsaturated ketone is set forth at lines 40–67 of columns 3 and 4 of Swiss Pat. No. 531,559. The formation of thio esters using thio acetic acid and unsaturated ketones is set forth at lines 15–20 of column 6 of Swiss Pat. No. 531,559.

U.S. Pat. No. 2,630,452 to Crouch, et al discloses processes for reacting unsaturated nitriles with thio acids whereby the thio ester moiety adds to the double bond at the "alpha" position with respect to the CN moiety using an aqueous alkali metal hydroxide catalyst or a quaternary ammonium compound catalyst. The substance of Crouch, et al may be illustrated by the following reaction betweeen acrylonitrile and thioacetic acid:

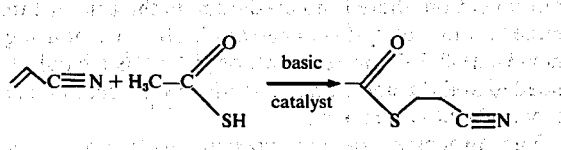

At column 2, lines 40–45, Crouch, et al states:

"In accomplishing the thioacetic acidacrylonitrile reaction, it has been found to be highly advantageous to employ certain basic catalysts as reaction promoters and directors. The preferred catalyst is a quaternary ammonium compound designated by the general formula . . ."

In Example IV of Crouch, et al, acrylonitrile is reacted with thioacetic acid in the presence of a t-butyl hydroperoxide catalyst at a temperature of 43°–49°C.

U.S. Pat. No. 3,441,589 to Oswald discloses reaction of thiol compounds such as mercaptans and thiolcarboxylic acids being selectively added to esters which, in turn, are formed by the reaction of maleic acid, fumaric acid or maleic anhydride with terminally unsaturated alcohols such as allyl alcohol at either of the terminal double bonds of the ester functionality or at the maleic or fumaric side of unsaturation with the use of either free radical or ionic catalysts. At column 7, Example 8, Oswald teaches the reaction of diallyl maleate with thiolacetic acid to form n-(3-acetylthio)-propyl allyl maleate according to the following reaction:

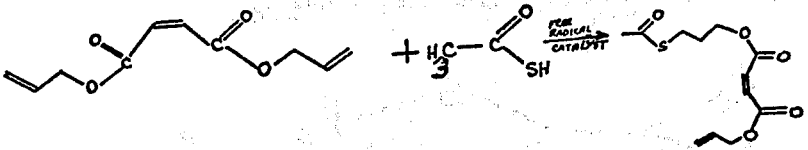

in the presence of a free radical catalyst, such as ultraviolet or gamma radiation or a "wide variety of peroxidic and azo compounds" (see column 3, lines 60–62).

Reid "Organic Chemistry of Bivalent Sulfur", Volume IV, 1962, Chemical Publishing Co., Inc.; discloses reactions of thioacetic acid with unsaturated compounds. At pages 15 and 16 Reid states:

"The most interesting reaction of thioacetic acid is its ready addition to unsaturates. An example of this is its addition to acrylonitrile. In this it exhibits its mercaptan character but in activity it far surpasses most mercaptans. Usually the addition takes place spontaneously and completely. With styrene the reaction is:

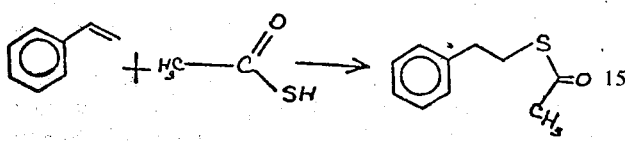

The product is the beta-phenethyl ester of thioacetic acid and is identical with that from phenethyl mercaptan and acetyl chloride . . . "

No teaching exists in the prior art to show that where $R_2$ is lower alkyl and $R_1$ is hydrogen, the effect of carrying out a reaction of a 2-ene-4-one-1-al with a thioacid (in the presence of base) is directive leading substantially to a reaction product where the thioester substitution is alpha to the ketone moiety and not the aldehyde moiety.

Furthermore, given the 2-ene-1,4-dione reactants of our invention, there is no prediction in the prior art that either (i) no catalyst is necessary in the case of using a hex-3-ene-2,5-dione reactant, or (ii) a basic catalyst is needed and the addition is directive in the case of using a pent-2-ene-4-one-1-al.

The processes of the present invention provide straightforward methods for producing 3-thia substituted alkane 1,4 diones in good yields in an economical manner.

Briefly, the processes of our invention comprise the steps of:

i. Providing a 2-ene-alkane 1,4 dione having the structure:

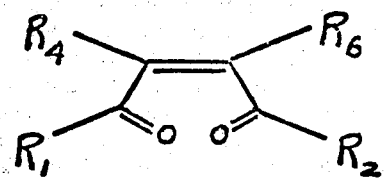

ii. Intimately admixing said 2-ene-alkane-1,4 dione with a sulfur compound having the formula:
$R_3SH$
thereby providing a substituted or unsubstituted 2-thia substituted 1,4 dione having the structure:

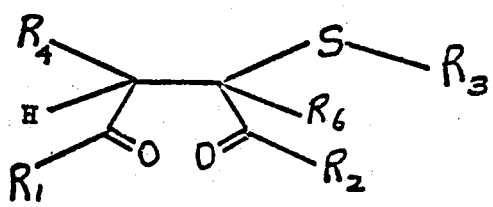

wherein
$R_3$ is selected from the group consisting of acyl and aroyl, wherein $R_2$ is lower alkyl; and wherein $R_1$, $R_4$ and $R_6$ are the same or different and are each selected from the group consisting of hydrogen and lower alkyl; wherein when $R_1$ is hydrogen, the reaction is carried out in the presence of an organic base; and wherein when $R_1$ is lower alkyl, the reaction is carried out in the absence of catalyst.

Two particularly novel features of our invention involve (i) addition of the thiol acids, either

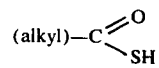

or

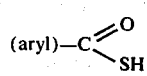

to a hex-3-ene-2,5-dione, e.g., having the structure:

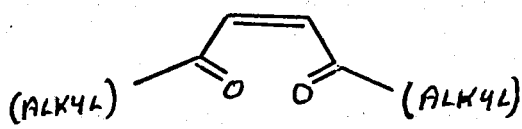

at room temperature in the absence of any catalyst to produce economic yields of 3-thia substituted alkane 1,4 dione, e.g., having the structure:

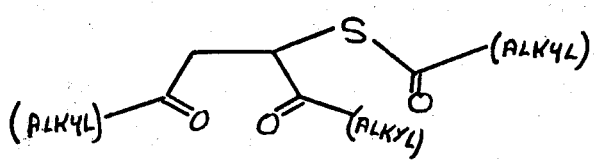

or

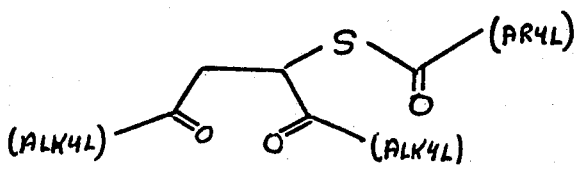

and (ii) addition of a thiol acid, either

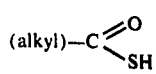

or

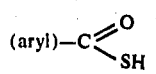

to pent-3-ene-4-one-1-als, e.g., having the structure:

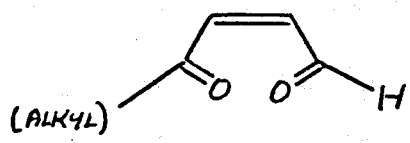

in the presence of an organic base to yield a 3-thia substituted pentane-4-one-1-al, e.g., having the structure:

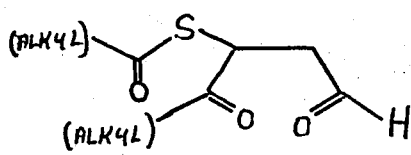

or

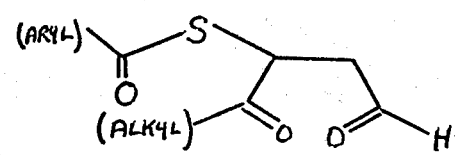

the addition being directive to that carbon atom (originally having the C=C double bond) which is "alpha" to the carbonyl group of the ketone moiety rather than the aldehyde moiety.

Examples of thio acids useful in our process are:
thioacetic acid
thiopropionic acid
thiobutyric acid
thioisobutyric acid
thio-n-pentenoic acid
thiocinnamic acid
thiobenzoic acid
2-methyl-thiobenzoic acid
3-methyl-thiobenzoic acid
4-methyl-thiobenzoic acid
2,4-dimethyl-thiobenzoic acid
3,5-dimethyl-thiobenzoic acid Whether an organic base is used or not in the reaction with the 2-ene-1,4 dione with the thio acid having the formula $R_3SH$, the 2-ene-1,4 dione can be exemplified as follows:

| Compound Name | $R_1$ | $R_2$ | $R_4$ |
|---|---|---|---|
| 3-Hexen-2,5-dione | Methyl | Methyl | Hydrogen |
| 3-Methyl-3-hexen-2,5 dione | Methyl | Methyl | Methyl |
| 3-Methyl-3-hepten-2,5 dione | Methyl | Ethyl | Methyl |
| 3-Ethyl-3-hepten-2,5-dione | Methyl | Ethyl | Ethyl |
| 4-Ethyl-4-octen-3,6 dione | Ethyl | Ethyl | Ethyl |
| 3-Propyl-3-hepten-2,5 dione | Methyl | Ethyl | Propyl |
| 4-Methyl-3-hepten-2,5 dione | Ethyl | Methyl | Methyl |
| 4-Methyl-4-octen-3,6-dione | Ethyl | Ethyl | Methyl |
| 4-Methyl-4-nonen-3,6-dione | Ethyl | Propyl | Methyl |
| 4-Propyl-3-hepten-3,6-dione | Ethyl | Methyl | Propyl |
| 5-Methyl-5-decen-4,7-dione | Propyl | Propyl | Methyl |
| 5-Methyl-4-nonen-3,6-dione | Propyl | Ethyl | Methyl |
| 4-Methyl-3-nonen-2,5-dione | Butyl | Methyl | Methyl |
| 4-Ethyl-3-nonen-2,5-dione | Butyl | Methyl | Ethyl |
| 3-Methyl-3-nonen-2,5-dione | Methyl | Butyl | Methyl |
| 3-Propyl-3-nonen-2,5 dione | Methyl | Butyl | Propyl |
| 3-Butyl-3-hexen-2,5-dione | Methyl | Methyl | Butyl |
| 4-Octen-3,6-dione | Ethyl | Ethyl | Hydrogen |

As stated above, $R_1$ and $R_2$ can each be hydrogen for the purposes of these processes of our invention in the event that in the reaction of the 2-ene-1,4 dione with the thioacid of the formula $R_3SH$, an organic base is used. Hence, in addition to the foregoing compounds, the following compounds can be utilized in the reaction with $R_3SH$:

| Compound Name | $R_1$ | $R_2$ | $R_4$ |
|---|---|---|---|
| 2-Buten-1,4-dial | Hydrogen | Hydrogen | Hydrogen |
| 2-Methyl-2-buten-1,4-dial | Hydrogen | Hydrogen | Methyl |
| 2-Pentenal-4-one | Methyl | Hydrogen | Hydrogen |
| 2-Hexenal-4-one | Ethyl | Hydrogen | Hydrogen |
| 3-Methyl-2-hexenal 4-one | Ethyl | Hydrogen | Methyl |
| 2-Methyl-2-pentenal 4-one | Hydrogen | Hydrogen | Methyl |
| 2-Methyl-2-heptenal 4-one | Hydrogen | Propyl | Methyl |
| 2-Methyl-2-octenal 4-one | Hydrogen | Butyl | Methyl |

Examples of useful organic bases are piperidine, pyridine, quinoline, triethyl amine and alpha-picoline.

The reaction may be carried out in a solvent such as water or an ether such as diethyl ether or a hydrocarbon such as benzene or hexane or cyclohexane. The reaction may also be carried out without the use of a solvent. The reaction may be carried out under reflux conditions although temperatures varying from 0° up to 60°C are suitable and will give rise to commercially suitable yields. When the reaction is carried out with highly volatile reactants, higher pressures than atmospheric pressure are preferred, e.g., three atmospheres pressure. Examples of reaction products, 3-thia-substituted-1,4-diones which are formed from the reaction of the 2-ene-1,4-diones with the thioacids, having the formula $R_3SH$ are as follows:

| 2-ene-1,4 dione Reactant | $R_3SH$ Reactant | 3-Thia Substituted 1,4-dione Reaction Product |
|---|---|---|
| 3-Hexen-2,5-dione | Thioacetic acid | 3-Thioacetyl-2,5-hexan-dione |
| 3-Methyl-3-hexen-2,5-dione | Thiopropionic acid | 3-Thiopropionyl-4-methyl hexan-2,5-dione |
| 3-Methyl-3-hepten-2,5-dione | Thiobenzoic acid | 4-Thiobenzoyl-4-methyl heptan-3,6-dione |
| 4-Ethyl-4-octen-3,6-dione | Thioacetic acid | 4-Thioacetyl-5-ethyl-octan-3,6- |

-continued

| 2-ene-1,4 dione Reactant | R₃SH Reactant | 3-Thia Substituted 1,4-dione Reaction Product |
|---|---|---|
| 2-Buten-1,4-dial | Thioacetic acid | 2-Thioacetyl-butan-1,4-dial |
| 2-Pentenal-4-one | 4-Methyl-thio benzoic acid | 3-Thiobenzoyl-pentenal-4-one |
| 2-Pentenal-4-one | Thioacetic acid | 3-Thioacetyl-pentenal-4-one |

The 2-thia substituted-1,4-diones as exemplified above are useful for altering the organoleptic properties of consumable materials, more particularly, foodstuffs. Thus, for example, 3-thioacetyl-2,5-hexanedione has a roasted meat aroma and a pot-roast and roasted meat flavor tested at levels of 5 ppm. Its flavor threshold value is at 1 ppm. The compound 3-thiobenzoyl-2,5-hexanedione has a berry and a meat aroma, an allium, earthy and horseradish flavor at concentrations of approximately 0.5 ppm. Its threshold value is at 0.5 ppm. 3-Thiobenzoyl-2,5-hexanedione at 5 ppm evaluated in beef bouillon has a meaty note. 3-Thioacetyl-2,5-hexanedione at 5 ppm adds a burnt meat note to beef bouillon. 3-Thiobenzoyl-2,5-hexanedione adds a slight green chicken meat note to chicken broth at 2.5 ppm. 3-Thioacetyl-2,5-hexanedione adds eggy chicken notes to chicken broth at 2.5 ppm.

The products of the process of our invention may be used as reaction intermediates and, when used as such, the thia-substituted 1,4-diones produced by the process of our invention are then cyclized to form substituted or unsubstituted 3-thiafurans according to the following reaction:

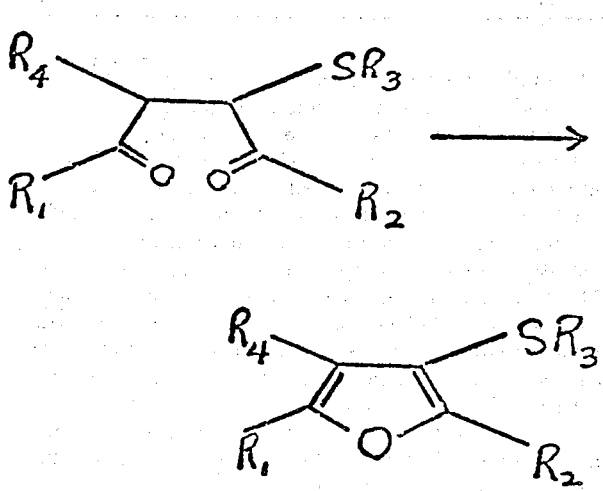

wherein $R_1$ and $R_2$ are the same or different and are each hydrogen or lower alkyl; wherein $R_3$ is either acyl or aroyl and $R_4$ is hydrogen or lower alkyl. The resulting 3-thiafurans may be used as such for their organoleptic properties or they may be hydrolyzed and then reacylated or aroylated to form other acyl thia or aroyl thia substituted furans which have still other organoleptic properties useful for flavoring foodstuffs.

The compound having the structure:

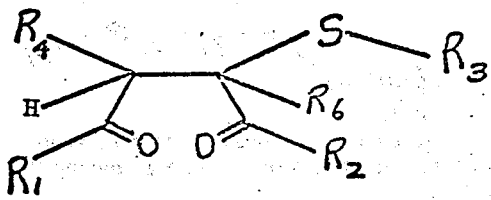

may also be intermediates in that they may be hydrolyzed first using a weak base (e.g., 2-5% aqueous NaOH, LiOH or KOH) and then neutralizing with acid to a pH of 5-6 to form compounds having the structure:

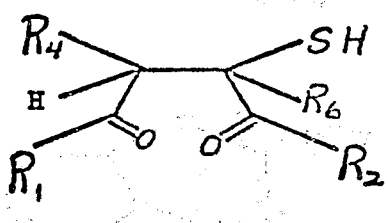

which have useful organoleptic properties. Thus, for example, 3-thioacetyl-2,5-hexanedione is hydrolyzed to 3-mercapto-2,5-hexanedione by treating the 3-thioacetyl compound first with 2% aqueous NaOH and then adjusting the pH to about 5 using 10% HCl. Hydrolysis conditions are preferably atmospheric pressure and 20°–50°C with ambient temperature being most convenient and economical.

The 3-thia alkane-1,4 dione derivatives and mixtures thereof produced according to the present invention can be used to alter, vary, fortify, modify, enhance, or otherwise improve the organoleptic properties, including flavor and/or aroma of a wide variety of materials which are ingested, consumed, or otherwise organoleptically sensed. The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such 3-thia alkane-1,4-dione derivatives are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods, including fish, crustaceans, mollusks, and the like, candies, breakfast foods, baked goods, vegetables, cereals, soft drinks, snack foods, dog and cat foods, other veterinary products, and the like.

When the 3-thia alkane-1,4 dione derivatives produced according to the process of this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

Examples of preferred co-flavoring adjuvants are:
Methyl thiazole alcohol (4-methyl-5-betahydroxyethyl thiazole);
2-Methyl butanethiol;
4-Mercapto-2-butanone;
3-Mercapto-4-pentanone;
1-Mercapto-2-propanone;
Benzaldehyde;
Furfural;
Furfural alcohol;
2-Mercapto propionic acid;
2-Pentene;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;
Hydrolyzed vegetable protein;
Hydrolyzed fish protein; and
Tetramethyl pyrazine The 3-thia alkane-1,4 dione derivatives, or the compositions incorporating them, as mentioned above, can be combined with one or more vehicles, or carriers for adding them to the particular product. Vehicles can be edible or otherwise suitable materials such as ethyl alcohol, propylene glycol, water, and the like. Carriers include materials such as gum arabic, carrageenan, other gums, and the like. The 3-thia alkane-1,4 dione compounds according to this invention can be incorporated with the carriers by conventional means such as spray-drying, drum-drying, and the like. Such carriers can also include materials for coacervating the 3-thia alkane-1,4 dione derivatives (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

The quantity of 3-thia alkane-1,4 dione derivatives or mixtures thereof utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product comsumed. The quantity used will vary depending upon the ultimate foodstuff; the amount and type of flavor initially present in the foodstuff; the further process of treatment steps to which the foodstuff will be subjected; regional and other preference factors; the type of storage, if any, to which the product will be subjected, and the preconsumption treatment, such as baking, frying, and so on, given to the product by the ultimate consumer. Accordingly, the terminology "effective amount" and "sufficient amount" is understood in the context of the present invention to be quantitiatively adequate to alter the flavor of the foodstuff.

It is accordingly preferred that the ultimate compositions contain from about 0.02 parts per million (ppm) to about 250 ppm of 3-thia-alkane-1,4 dione derivative or derivatives. More particularly, in food compositions it is desirable to use from 0.05 ppm to 100 ppm for enhancing flavors and in certain preferred embodiments of the invention, from about 0.2 to 50 ppm of the derivatives are included to add positive flavors to the finished product. All parts, proportions, percentages, and ratios herein are by weight unless otherwise indicated.

The amount of 3-thia alkane-1,4 dione material or materials of our invention to be utilized in flavoring compositions can be varied over a wide range depending upon the particular quality to be added to the foodstuff. Thus, amounts of one or more derivatives according to the present invention of from about 2 ppm up to 80 or 90 percent of the total flavoring composition can be incorporated in such compositions. It is generally found to be desirable to include from about 10 ppm up to about 0.1 percent of the 3-thia alkane-1,4 dione derivatives in such compositions.

The following examples I, II, V, VI, VII and X are given to illustrate embodiments of the invention as it is preferably preferred to practice it. Examples III, IV, VIII and IX are given to illustrate the usefulness of the products produced by the process of our invention. It will be understood that these examples are illustrative and the invention is not to be considered as restricted thereto except as indicated in the appended claims.

EXAMPLE I (PREPARATION OF CIS-3-HEXENE-2,5-DIONE)

In a 1000 ml round bottom flask fitted with condenser and magnetic stirrer are placed 200 g of 2,5-dimethoxy-2,5-dimethyl-2,5-dihydrofuran and 200 ml of a 1% aqueous acetic acid solution. The resulting solution is heated to reflux, refluxed for 2 minutes, cooled with an ice bath to 25°C and 625 ml of a 2% sodium bicarbonate solution is added. The solution is saturated by addition of 23 g of sodium chloride and extracted with methylene chloride (1 × 200 ml and 3 × 100 ml). After drying over sodium sulfate removal of the methylene chloride in vacuo gives 142 g of crude cis-3-hexene-2,5-dione which by GLC analysis is about 90% product having the structure:

EXAMPLE II (PREPARATION OF 3-THIOACETYL-2,5-HEXANEDIONE)

In a 1000 ml round bottom flask fitted with magnetic stirrer, thermometer, addition funnel and reflux condenser are placed 142 g of crude cis-3-hexene-2,5-dione (ex Example I), 380 ml of ether and 5 drops of piperidine. Thio acetic acid (96.6 g) is added over a period of one hour. When about ⅛ of the thio acetic acid is added, the solution begins to reflux which continues during the remainder of the addition. After addition is complete, the mixture is allowed to stand for 85 minutes. Ether is then removed in vacuo (water aspirator) to give 235 g of crude material containing about 91% 3-thioacetyl-2,5-hexanedione. Distillation of a 134 g portion of the crude gives 84.5 g of 3-thioacetyl-2,5-hexanedione boiling at 86° to 87°C at 0.5 torr. NMR, IR and mass spectral analyses confirm the structure:

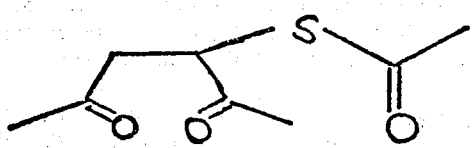

EXAMPLE III (PREPARATION OF 3-PROPYLTHIO-2,5-HEXANEDIONE)

In a 500 ml flask fitted with thermometer, addition funnel, reflux condenser and magnetic stirrer are placed 95 ml of ether, 35.4 g of cis-3-hexene-2,5-dione and one drop of piperidine. Addition of 24 g of n-propanethiol is started and as the addition progresses more piperidine is added (33 drops total) periodically. After standing 18 hours, the solution is washed successively with two 7.5 ml portions of 10% hydrochloric acid, saturated sodium chloride solution (10 ml), 5% sodium bicarbonate solution and two 10 ml portions of saturated sodium chloride solution. The ether solution is dried over sodium sulfate and concentrated to give 51.4 g of a dark yellow oil. Analysis by GLC shows the material to be essentially pure 3-thiopropyl-2,5-hexanedione. Mass spectral analysis shows molecular ion 188 then descending order 43, 103, 41, 145, 71, 114 and 61 m/e units.

EXAMPLE IV (PREPARATION OF 3-MERCAPTO-2,5-HEXANEDIONE)

To 150 ml of a 2% sodium hydroxide solution in a flask fitted for stirring is added 10 g of 3-thioacetyl-2,5-hexanedione. After stirring for one hour the pH of the mixture is adjusted to 5–6 by the addition of dilute (10%) hydrochloric acid, the solution is saturated with sodium chloride solution and extracted with ether (4 × 25 ml). The ether extracts are combined, washed with saturated sodium chloride solution (15 ml), dried and concentrated in vacuo to give 6.2 g of crude 3-mercapto-2,5-hexanedione. Vacuum distillation gives 2.5 g of 3-mercapto-2,5-hexanedione boiling at 57°–59°C at 0.85 torr. NMR, IR and mass spectral analyses confirm the structure as 3-mercapto-2,5-hexanedione.

EXAMPLE V (PREPARATION OF 2-THIOACETYL-1,4-BUTANE-DIAL)

A. Preparation of 2-butene-1,4-dial

A mixture of 2,5-dimethoxy-2,5-dihydrofuran (20 g), water (80 ml) and acetic acid (3 drops) is stirred for 105 minutes at room temperature, 22 minutes at 40°C and 90 minutes between 60°C and 75°C. GLC analysis at this point indicates 15.7% starting material and 83.5% 2-butene-1,4-dial. The mixture is cooled to 25°C and sodium bicarbonate (0.3 g) is added.

B. Preparation of 3-thioacetyl-1,4-butanedial

To the aqueous solution obtained in Section A supra, is added 10 g of thio acetic acid during a 14 minute period. During the addition, the temperature is kept below 30°C by intermittent application of a cooling bath. After 110 minutes, the reaction mixture is extracted with methylene chloride (3 × 35 ml). The combined methylene chloride extracts are dried and then concentrated in vacuo to give 17.8 g of yellow oil containing about 80% 2-thioacetyl-1,4-butanedial. The compound is identified through mass spectral, NMR and IR analyses as having the structure:

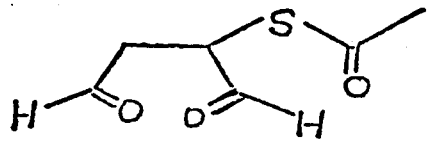

M.S. - No molecular ion; remaining peaks in decreasing
intensity - 43, 29, 27, 45, 55, 60, 84, 100
and 142 m/e units.
NMR (CDCl$_3$) 2.38 (s,3) 3.02 (multiplet 2,J=10H$_z$),
4.46 (r,1J=10H$^z$) 9.40 (s,1) and
9.68 (s,1) ppm.
IR (thin film) - 2850, 2750, 1720, 1700 (shoulder),
1388, 1352, 1132 and 958 cm$^{-1}$.

EXAMPLE VI (PREPARATION OF 3-THIOACETYL-4-OXO-PENTANAL)

A. 4-oxo-2-pentenal

Into a 5 liter, three-necked flask fitted with mechanical stirrer, thermometer and vacuum take-off are placed 600 g of 2-methyl-2,5-dimethoxy-2,5-dihydrofuran and 2400 ml of deionized water. After 20 minutes of stirring at room temperature, the mixture becomes homogeneous and has a pale yellow green color. Analysis of a sample of the reaction mixture by GLC after 3.25 hours shows 22% methanol, 67% 4-oxo-2-pentenal and 9% starting material. Vacuum (26 torr.) is applied to the reaction mixture while maintaining the temperature of the reaction mixture between 25° and 30°C. After 3.25 hours GLC analysis shows 13% methanol, 82% 4-oxo-2-pentenal and 3.2% starting material. The vacuum is removed and the reaction mixture is allowed to stand at room temperature overnight. Analysis after standing overnight shows 12.9% methanol, 85% 4-oxo-2-pentenal and 2.1% starting material.

B. 3-thioacetyl-4-oxo-pentanal

In a 5 liter, three-necked flask fitted with mechanical stirrer, thermometer and addition funnel are placed 2325 ml of the solution obtained in (A) and 2 ml of piperidine diluted in 5 ml of water. To this solution is added a mixture of thio acetic acid (292.3 g) and piperidine (13 ml) over a 20 minute period. After standing an additional 10 minutes, 20 ml of concentrated hydrochloric acid is added, the resulting mixture poured into a separatory funnel and the oil layer removed. The aqueous layer is extracted with benzene (500 ml) and methylene chloride (2 × 500 ml). The benzene extract is combined with the oil layer and the mixture is dried over sodium sulfate. The methylene chloride extracts are combined and dried over sodium sulfate. Solvent removal in vacuo (40°–45°C both at 15 torr.) gives 414.5 g of crude oil from the benzene extract and 172.5 g of crude oil from the methylene chloride extracts. The crude oil is distilled under vacuum to give 3-thioacetyl-4-oxo-pentanal boiling at 94°–98°C at 0.3–0.55 mm Hg.

EXAMPLE VII (PREPARATION OF 3-THIOBENZOYL-2,5-HEXANEDIONE)

In a 50 ml three-necked flask equipped with thermometer, 10 ml addition funnel and magnetic stirrer is placed 6 g of 2,5-dimethoxy-2,5-dimethyl-2,5-dihydrofuran, 24 ml H$_2$O and 1 drop of glacial acetic acid. The mixture (which is crude cis-3-hexene-2,5-dione) is stirred for one hour until homogeneous. Then 5.25 g thiobenzoic acid is added over a five-minute period. The mixture is allowed to stand for eighteen more minutes and is then extracted with 35 ml of methylene chloride. After drying over anhydrous sodium sulfate and subsequent solvent removal, 7.55 g of crude 3-thiobenzoyl-2,5-hexanedione is recovered. The crude material is purified by column chromatography on 108 g silicic acid packed in ether:hexane (1:9) mixture. Elution with 630 ml ether:hexane (1:9) solvent mixture; followed by elution with 500 ml ether:hexane (1:4) solvent mixture; followed by elution with 850 ml ether:hexane (1:3) solvent mixture gives 6.2 g of 3-thiobenzoyl-2,5-hexanedione, having the following analyses:

MS - Parent Ion, then decreasing order: 250, 105, 77, 43, 128, 106.

NMR (CDCl$_3$): 7.96 (d,1,J=2 Hz),
7.88 (d,1,J=2 Hz),
7.48 (m,3),
4.78 (q,1,J=5 Hz),
3.06 (m,2),
2.29 (s,3),
2.14 (s,4) ppm IR (KBr plate, thin film): 3060, 3000, 2960, 2910, 1709, 1661, 1590, 1578, 1445, 1355, 1204, 1172 1154, 900, 759, 681, 640 cm$^{-1}$

EXAMPLE VIII

The following formulation is prepared:

| Ingredient | Parts by Weight |
|---|---|
| Liquid hydrolyzed vegetable protein | 90.00 |
| 4-Methyl-5-beta-hydroxy-ethyl thiazole | 5.00 |
| Tetrahydro thiophene-3-one | 1.00 |
| Furfuryl mercaptan | 0.01 |
| 2-nonenal | 0.50 |
| Difurfuryl disulfide | 0.49 |
| Dimethyl sulfide | 0.50 |
| Methyl mercaptan | 0.50 |
| 3-Thioacetyl-2,5-hexanedione | 2.00 |

The 3-thioacetyl-2,5-hexanedione imparts a roasted meat taste to the above formula and ties in and rounds up the other meat-like chemicals in the formula. When 3-thioacetyl-2,5-hexanedione is replaced by 3-thiobenzoyl-2,5-hexanedione, a similar effect is imparted to the over-all flavor and aroma pattern of the above formula.

EXAMPLE IX (PREPARATION OF 3-THIOISOVALERYL-2,5-HEXANEDIONE)

In a 250 ml three-necked flask fitted with magnetic stirrer, reflux condenser and addition funnel are placed 10 g (0.068 moles) of 3-mercapto-2,5-hexanedione, 5.4 g (0.068 moles) pyridine and 150 ml anhydrous diethyl ether. To this is added 8.3 g (0.068 moles) of isovaleryl chloride during a four minute period. The resulting ether solution is then washed, in sequence, with 150 ml of water, 50 ml of 4% HCl, 50 ml of saturated NaHCO$_3$ solution and dried over anhydrous sodium sulfate. Sovent removal in vacuo gives 13.2 g crude 3-thioisovaleryl 2,5-hexanedione.

Distillation of the crude gives 10.8 g product boiling at 108°–110°C at 0.8–0.9 mm Hg pressure and having the following analyses:

Mass Spectral Analysis - In decreasing order (no parent ion): 43, 57, 85, 128.

NMR Spectrum (CDCl$_3$)

| | |
|---|---|
| 4.60 | (q,1) |
| 2.95 | (m,5) |
| 2.32 | (s,3) |
| 2.17 | (s,3) |
| 0.99 | (d,6) ppm |

EXAMPLE X (PREPARATION OF 2-PROPYL-3-THIOACETYL FURAN)

A. Preparation of 2-propyl-2,5-dimethoxy-2,5-dihydro furan from 2-propyl furan

Reaction:

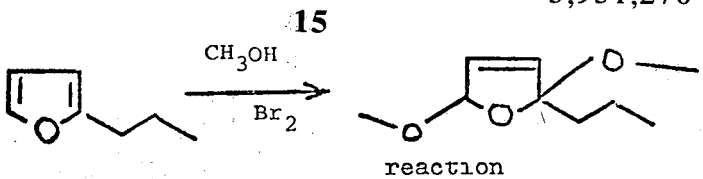

reaction

Into a 500 ml three-necked flask equipped with mechanical stirrer, calcium carbonate drying tube and thermometer, the following materials are placed:

| | | |
|---|---|---|
| (i) | 2-Propyl furan | 25.0 g (0.227 moles) |
| (ii) | Methanol, absolute | 180 ml |
| (iii) | Sodium carbonate | 47.1 g (0.454 moles) |

The reaction mass is cooled to −10°C using a dry-ice acetone bath. Over a period of 20 minutes, a solution of 36.3 grams of bromine in 70 ml absolute methanol is added dropwise while maintaining the reaction mass at −12°C to −13°C. After the addition of the bromine solution, the reaction mass is stirred for 1.5 hours while maintaining same at −10°C.

The reaction mass is then mixed with 450 ml of saturated sodium chloride solution. The resulting mixture is suction filtered and the filter cake is washed with 100 ml of methylene dichloride. The resultant filtrate and washings are placed in a separatory funnel and the lower organic phase is drawn off. The aqueous phase is extracted with two 100 ml portions of methylene dichloride and the organic solutions are combined. The organic solution is then dried over anhydrous sodium sulfate and filtered; and then concentrated in vacuo to a yellow liquid weighing 32.7 grams. The major peak of this material determined by GLC contains 2-propyl-2,5-dimethoxy-2,5-dihydro furan (GLC conditions: F & M 5750; 8 feet × ¼ inch SE-30; programmed from 130°-225°C at 4°C per minute, with an He flow rate of 80 ml/minute, chart speed 0.25 inch per minute).

B. Preparation of 4-oxo-2-heptenal

Reaction:

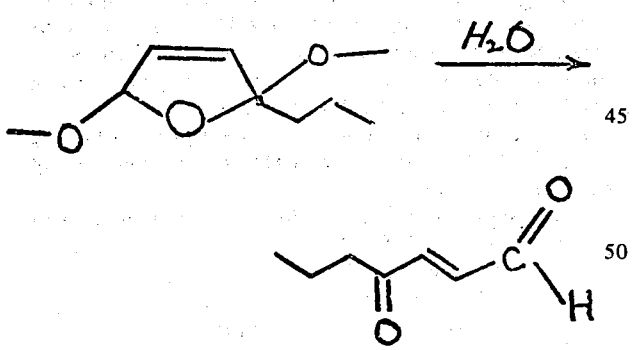

Into a 250 ml three-necked reaction flask equipped with mechanical stirrer and thermometer the following materials are added:

| | | |
|---|---|---|
| (i) | 2-Propyl-2,5-dimethoxy 2,5-dihydrofuran prepared according to the process of Part A | 32.7 g (0.16 moles) |
| (ii) | Water (distilled) | 325 ml |

The reaction mass is stirred for a period of 4 hours at 24°C. At the end of this period of time, the reaction mass exists in two phases; an aqueous upper phase and an organic lower phase. The aqueous upper phase is decanted and placed in a 1 liter vessel for the following reaction C.

C. Reaction of 4-oxo-heptenal with thioacetic acid

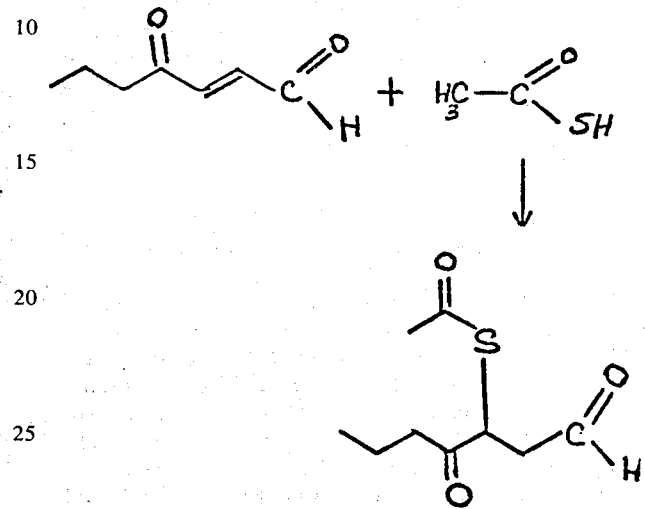

To the stirred aqueous solution produced in Part B, supra, of 4-oxo-2-heptenal is added 0.4 ml piperidine. After the piperidine addition, 12.4 grams of thioacetic acid is added to the reaction mass over a period of 4 minutes while maintaining the reaction mass at a temperature in the range of 27°–32°C. After the thioacetic acid addition is complete, the reaction mass is stirred for 1.5 hours. The reaction mass is then placed in a separatory funnel and extracted with 100 ml of methylene dichloride. The methylene dichloride solution is then separated, dried over anhydrous sodium sulfate and concentrated to an orange oil weighing 23.8 grams. This orange oil is analyzed using GLC, NMR and IR analyses and determined to be substantially 3-thioacetyl-4-oxo-heptenal-1.

Mass Spectral Analysis:

Molecular Ion, then in decreasing intensity: 202, 43, 28, 71, 55, 41, 97, 83 m/e.

D. Preparation of 2-propyl-3-thioacetyl furan

Reaction:

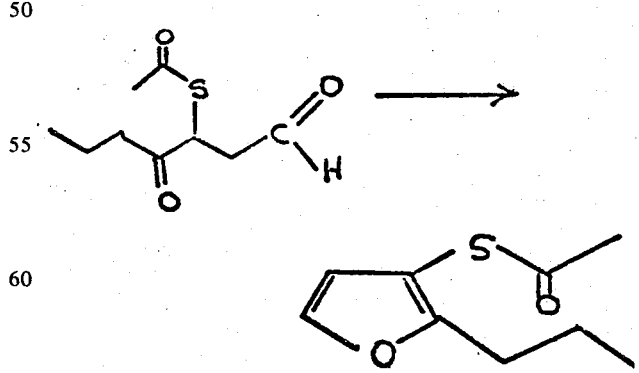

Into a 500 ml flask, equipped with reflux condenser, calcium chloride drying tube, mechanical stirrer, thermometer and addition funnel, the following materials are placed:

| | |
|---|---|
| (i) Isopropenyl acetate | 175 ml |
| (ii) Concentrated sulfuric acid | 0.5 ml |

The mass is heated to reflux (93°C) and, over a period of 20 minutes, while maintaining the reaction mass temperature at 91°–93°C, a solution of 23.0 grams of the reaction product of Part C in 25 ml of isopropenyl acetate is added from the addition funnel to the reaction mass with stirring. The reaction mass is then stirred and maintained at 91°C for a period of 30 minutes at which point 5.0 grams of sodium bicarbonate is added to the mass.

The isopropenyl acetate cyclization agent is then distilled off at a pot temperature of 80°C and a head temperature of 50°C at 60 mm Hg pressure. The resulting residue is admixed with 50 ml benzene and 50 ml water. The resulting mixture is placed into a separatory funnel and the layers are separated. The benzene layer is filtered through anhydrous sodium sulfate and is then concentrated in vacuo to a brown liquid weighing 5.0 grams. This liquid is distilled through a short path microdistillation apparatus at 100°–103°C and 0.3 mm Hg pressure, yielding 2-propyl-3-thioacetylfuran as confirmed by mass spectral and NMR analyses.

Mass Spectral Analysis:

Molecular Ion, then in decreasing intensity: 184, 113, 43, 142, 27, 184.

NMR Analysis ($CDCl_3$)

| Signal | Interpretation |
|---|---|
| δ1.01 (t,3) | $CH_2CH_3$ |
| 1.65 (m,2) | $CH_2CH_2CH_3$ |
| 2.36 (s,3) | $-\overset{O}{\underset{\|}{C}}-CH_3$ |
| 2.59 (t,2) | |
| 6.32 (d,1) | |
| 7.35 ppm (d,1) | |

What is claimed is:

1. A process for producing a substituted or unsubstituted 3-thia alkane-4-one-1-al comprising the step of intimately admixing an alk-2-ene-4-one-1-al having the structure:

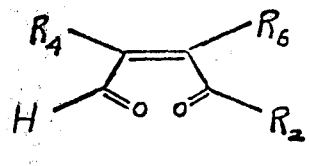

with a sulfur compound having the formula
$R_3SH$
in the presence of an organic base selected from the group consisting of secondary amines and tertiary amines thereby providing a substituted or unsubstituted 3-thia alkane-4-one-1-al having the structure:

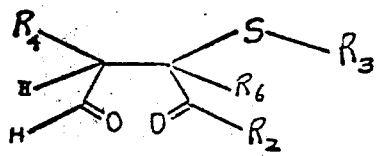

wherein $R_3$ is selected from the group consisting of acetyl and benzoyl; wherein $R_2$ is lower alkyl; and wherein $R_4$ and $R_6$ are the same or different and are each selected from the group consisting of hydrogen and lower alkyl.

2. The process of claim 1 wherein the organic base is selected from the group consisting of piperidine, pyridine, triethyl amine, quinoline and alpha-picoline.

3. The process of claim 1 wherein $R_6$ is hydrogen and $R_2$ is methyl.

4. The process of claim 3 wherein $R_3$ is benzoyl.

5. The process of claim 3 wherein $R_3$ is acetyl.

6. The process of claim 3 wherein $R_4$ is hydrogen.

7. The process of claim 3 wherein $R_4$ and $R_6$ are each hydrogen; $R_2$ is methyl.

* * * * *

UNITED STATES PATENT AND TRADEMARK OFFICE
CERTIFICATE OF CORRECTION

PATENT NO. : 3,931,270
DATED : January 6, 1976
INVENTOR(S) : William J. Evers, Bernard J. Mayers It is certified that error appears in the above—identified patent and that said Letters Patent are hereby corrected as shown below:

Title Page, under [75], correct inventors to read:

William J. Evers, Middletown;

Howard H. Heinsohn, Jr., Hazlet;

Bernard J. Mayers, Cliffwood

Beach, all of N.J.

Signed and Sealed this

Thirty-first Day of August 1976

[SEAL]

Attest:

RUTH C. MASON
*Attesting Officer*

C. MARSHALL DANN
*Commissioner of Patents and Trademarks*